(12) United States Patent
Stalcup et al.

(10) Patent No.: US 12,329,645 B2
(45) Date of Patent: Jun. 17, 2025

(54) METHODS OF FORMING IMPLANTS USING HEAT BONDING

(71) Applicant: SMed-TA/TD, LLC, Columbia City, IN (US)

(72) Inventors: Gregory C. Stalcup, Fort Wayne, IN (US); Joseph W. Jurick, Fort Wayne, IN (US)

(73) Assignee: SMed-TA/TD, LLC, Columbia City, IN (US)

( * ) Notice: Subject to any disclaimer, the term of this patent is extended or adjusted under 35 U.S.C. 154(b) by 522 days.

(21) Appl. No.: 16/858,007

(22) Filed: Apr. 24, 2020

(65) Prior Publication Data
US 2020/0330232 A1 Oct. 22, 2020

Related U.S. Application Data

(63) Continuation of application No. 16/850,442, filed on Apr. 16, 2020.
(Continued)

(51) Int. Cl.
*A61F 2/30* (2006.01)
*A61F 2/28* (2006.01)
(Continued)

(52) U.S. Cl.
CPC .............. *A61F 2/3094* (2013.01); *A61F 2/28* (2013.01); *A61F 2/30771* (2013.01); *B29C 65/006* (2013.01); *B29C 65/02* (2013.01); *A61F 2002/30784* (2013.01); *A61F 2002/3093* (2013.01); *A61F 2002/30967* (2013.01); *A61F 2002/30968* (2013.01);
(Continued)

(58) Field of Classification Search
CPC .......... A61F 2/3094; A61F 2002/30967; A61F 2310/00023; A61F 2310/00029; A61F 2310/00017; A61F 2002/30968; A61F 2002/3093; A61F 2002/30784; A61F 2/30771; A61F 2/28; B29C 65/02; B29C 65/006
See application file for complete search history.

(56) References Cited

U.S. PATENT DOCUMENTS 8,821,582 B1 9/2014 Lyren
2007/0129809 A1 6/2007 Meridew et al.
(Continued)

FOREIGN PATENT DOCUMENTS

EP 0 623 687 A2 11/1994
EP 3 725 270 A1 10/2020
WO 2012/065068 A1 5/2012

OTHER PUBLICATIONS

Extended European Search Report dated Sep. 3, 2020 for European Patent Application No. 20170013.5 (8 pages).
(Continued)

*Primary Examiner* — Vishal I Patel
*Assistant Examiner* — Christine L Nelson
(74) *Attorney, Agent, or Firm* — TAYLOR & EDELSTEIN, PC

(57) ABSTRACT

A method of forming an orthopaedic implant includes: placing a bonding portion of a mating part in an opening formed in an implant body, the opening defining a variable
(Continued)

opening width; and heat bonding the bonding portion to the material to bond the mating part to the implant body.

11 Claims, 10 Drawing Sheets

Related U.S. Application Data

(60) Provisional application No. 62/835,600, filed on Apr. 18, 2019.

(51) Int. Cl.
*B29C 65/00* (2006.01)
*B29C 65/02* (2006.01)

(52) U.S. Cl.
CPC ............... *A61F 2310/00017* (2013.01); *A61F 2310/00023* (2013.01); *A61F 2310/00029* (2013.01)

(56) References Cited

U.S. PATENT DOCUMENTS

| | | |
|---|---|---|
| 2010/0042218 A1 | 2/2010 | Nebosky et al. |
| 2013/0211541 A1 | 8/2013 | Kerr et al. |
| 2014/0277547 A1* | 9/2014 | Rybolt ................... A61F 2/389 |
| | | 29/445 |
| 2015/0320561 A1 | 11/2015 | Noble |
| 2016/0008102 A1* | 1/2016 | Lomicka ................ A61C 8/006 |
| | | 433/201.1 |
| 2018/0289493 A1 | 10/2018 | Mansmann |
| 2018/0296349 A1 | 10/2018 | Stalcup et al. |
| 2020/0179122 A1* | 6/2020 | Stalcup ............... A61F 2/30771 |

OTHER PUBLICATIONS

Japanese Office Action dated Jan. 4, 2024 for Japanese Patent Application No. 2020-074292 (5 pages).
English translation of Japanese Office Action dated Jan. 4, 2024 for Japanese Patent Application No. 2020-074292 (9 pages).

* cited by examiner

METHODS OF FORMING IMPLANTS USING HEAT BONDING

CROSS REFERENCE TO RELATED APPLICATIONS

This is a continuation of U.S. patent application Ser. No. 16/850,442, entitled "METHODS OF FORMING IMPLANTS WITH POROUS SURFACES USING HEAT BONDING", filed Apr. 16, 2020, which is incorporated herein by reference. U.S. patent application Ser. No. 16/850,442 is a non-provisional application based upon U.S. provisional patent application Ser. No. 62/835,600, entitled "METHODS OF FORMING IMPLANTS WITH POROUS SURFACES USING HEAT BONDING", filed Apr. 18, 2019, which is incorporated herein by reference.

BACKGROUND OF THE INVENTION

1. Field of the Invention

The present invention relates to methods of forming implants, and, more particularly, to methods of forming implants using heat bonding.

2. Description of the Related Art

Orthopaedic implants often have complex shapes that are difficult to produce. The difficulty in producing the orthopaedic implants contributes significantly to the final cost of the orthopaedic implants.

What is needed in the art is a way to form orthopaedic implants in a less expensive manner than known ways.

SUMMARY OF THE INVENTION

Exemplary embodiments disclosed herein provide a method of forming an orthopaedic implant including heat bonding a bonding portion of a mating part to an implant body, the bonding portion being disposed in a variable width opening of the implant body.

In some exemplary embodiments provided according to the present invention, a method of forming an orthopaedic implant includes: placing a bonding portion of a mating part in an opening formed in an implant body, the opening defining a variable opening width; and heat bonding the bonding portion to the material to bond the mating part to the implant body.

In some exemplary embodiments provided according to the present invention, an orthopaedic implant includes: an implant body having an opening formed therein, the opening defining a variable width; and a mating part including a bonding portion disposed in the opening and heat bonded to the implant body.

One possible advantage that may be realized by exemplary embodiments disclosed herein is that disposing the bonding portion in the variable width opening and heat bonding the bonding portion to the implant body can form a mechanical interlock, in addition to the heat bond, to increase the bond strength.

Another possible advantage that may be realized by exemplary embodiments disclosed herein is that multiple mating parts and implant bodies can be produced separately before being joined at the same time to rapidly manufacture multiple orthopaedic implants.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
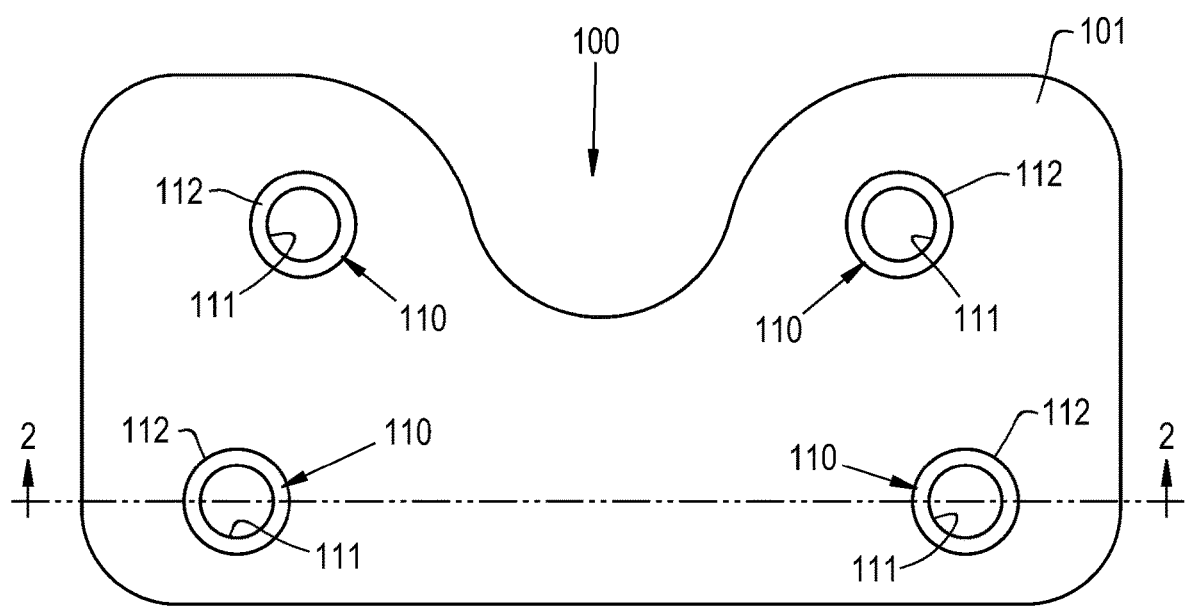
FIG. 1 is a top view of an exemplary embodiment of an orthopaedic implant including bonded inserts heat bonded to an implant body, provided according to the present invention.

Referring now to the drawings, and more particularly to FIG. 1, an exemplary embodiment of an orthopaedic implant 100 formed according to the present disclosure is illustrated. The implant 100 may take the form of a tibial implant, a femoral implant, an acetabular implant, a glenoid implant, a dental implant, or any other type of medical or veterinary implant. The orthopaedic implant 100 includes a base 101, which may also be referred to as an "implant body," with a plurality of inserts 110 bonded to the base 101. Each of the inserts 110 may be, for example, a peg with an exposed surface 111 that is at least partially covered with porous ingrowth material 112 and sized and shaped for insertion into an opening formed in a bone or other tissue. In some embodiments, the inserts 110 consist of one or more porous ingrowth materials without an underlying substrate. The inserts 110 may comprise, for example, a metal such as titanium, stainless steel, or cobalt chrome or a polymer such as polyether ether ketone. The porous ingrowth material 112 may be, for example, a porous metal or polymer material with pore geometry that is selected to encourage tissue ingrowth into the ingrowth material. Exemplary porous ingrowth materials that may be utilized include materials sold under the trade name OSTEOSYNC® by SITES MEDICAL® of Columbia City, Indiana Each of the inserts 110 may be bonded to a bottom surface of the base 101, which may also be at least partially covered by porous ingrowth material to encourage fixation of the implant.

Figure 2:
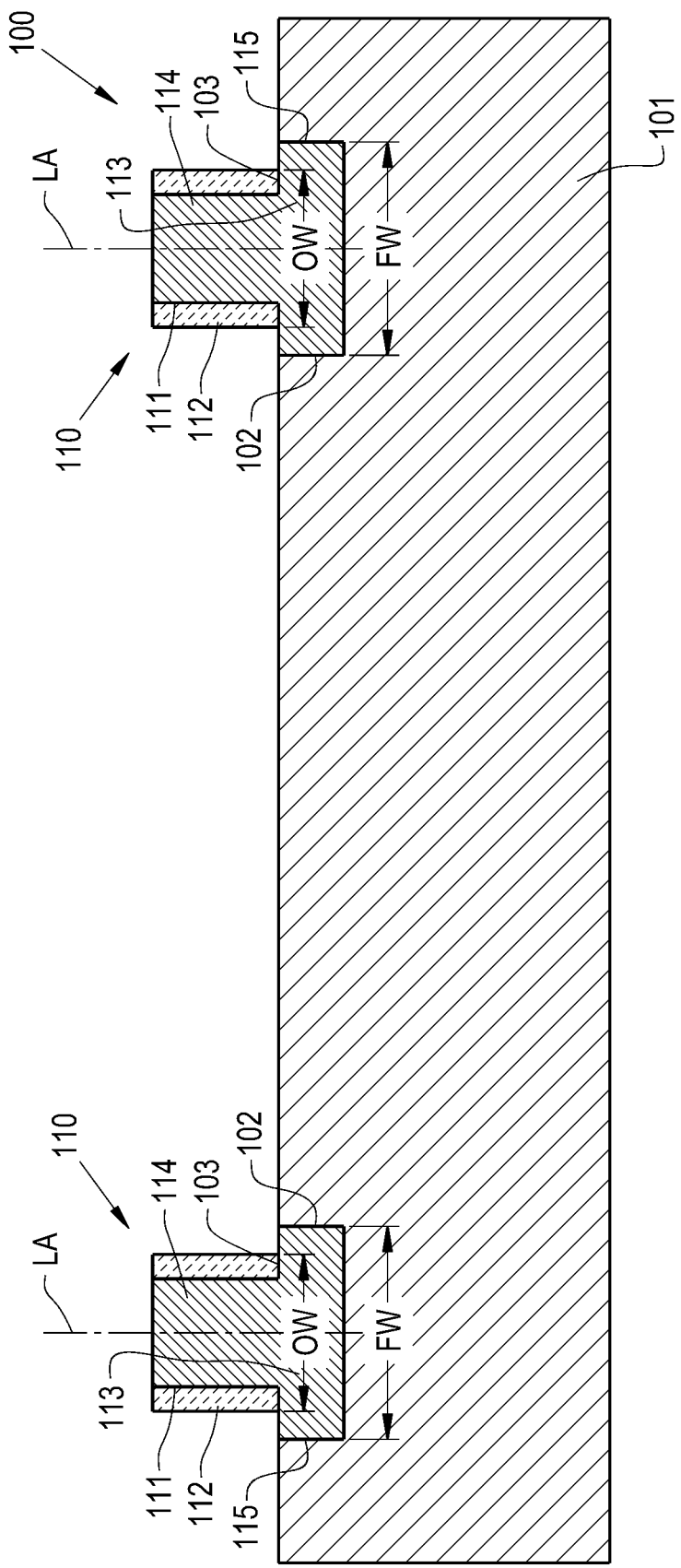
FIG. 2 is a cross-sectional view of the orthopaedic implant of FIG. 1 taken along line 2-2.

Referring now to FIG. 2 as well, a cross-section through the implant 100 and some of the bonded inserts 110 is illustrated. The inserts 110 may each include a bare portion 113 placed inside a respective opening 102 formed in material of the base 101 and a bonded portion 114 that is bonded to the porous ingrowth material 112. As used herein, the portion 113 is "bare" in the sense that it does not include the porous ingrowth material 112, but it can still include, for example, a surface coating to resist corrosion of the material. The bare portion 113 of the inserts 110 may include a flange 115 that extends perpendicularly away from a longitudinal axis LA of the insert 110 and defines a widest portion of the insert 110. The longitudinal axis LA may extend through the bonded portion 114 of the insert 110, which includes the surface 111 that is bonded to the porous ingrowth material 112. In some embodiments, the flange 115 is also at least partially covered by porous ingrowth material and/or includes threads 116 that can thread into corresponding threads of the opening 102 to form a mechanical interlock prior to heat bonding.

As can be seen in FIG. 2, the opening 102 formed in the material can define an opening width OW that is less than a width FW of the flange 115 to prevent easy removal of the flange 115 from the opening 102 once the flange 115 is placed therein. The opening 102 may also be defined by a plurality of walls 104 that perpendicularly extend from a bottom surface 105, which defines the closed bottom of the opening 102, i.e., in some embodiments the opening 102 is not fully formed through the base/implant body 101. As can be appreciated from the exemplary embodiment of an orthopaedic implant 300 illustrated in FIG. 3, an implant body 301 may also be provided with an opening 302 that defines an opening width OW2 that is the same, or slightly greater as illustrated, than the width FW of the flange 115. When the flange 115 is placed in the opening 102, 302, the porous ingrowth material may abut against walls 103, 303 of the opening 102, 302 and/or abut against a surface of the material in which the opening 102, 302 is formed so the porous ingrowth material 112 substantially covers the opening 102.

Figure 3:
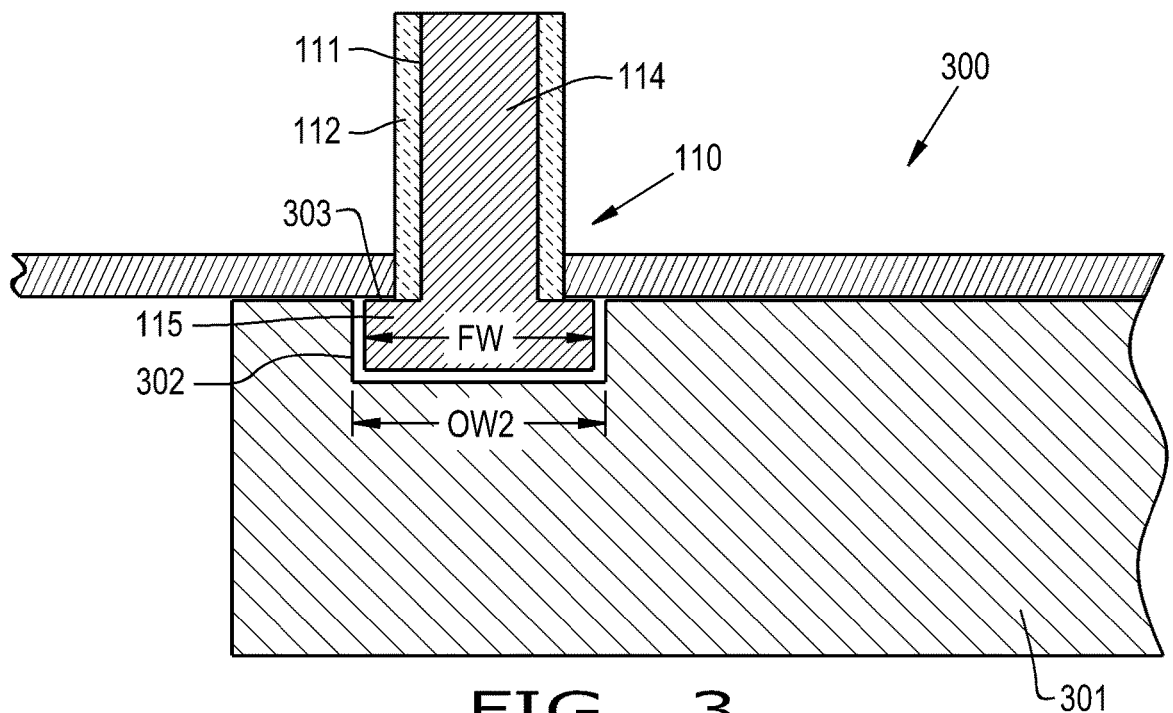
FIG. 3 is a cross-sectional view of another exemplary embodiment of an orthopaedic implant including a bonded insert heat bonded to an implant body with an opening that is relatively large, provided according to the present invention.
Figure 4:
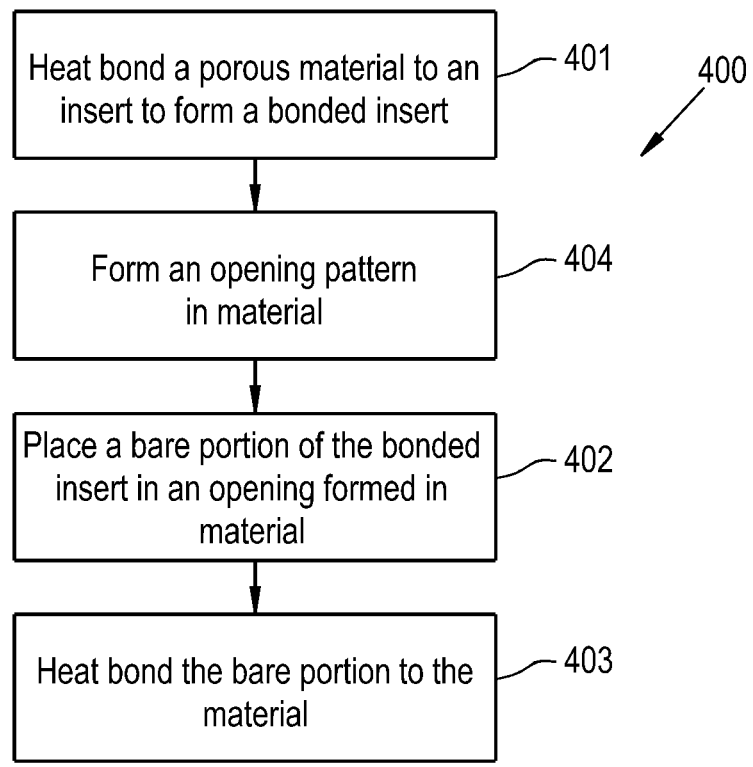
FIG. 4 is a flow chart illustrating an exemplary embodiment of a method of forming an orthopaedic implant provided according to the present invention.

To form the implant 100, 300 illustrated in FIGS. 1-3, an exemplary embodiment of a method 400 of forming an implant is provided and illustrated in FIG. 4. The method 400 includes heat bonding 401 a porous material, such as the previously described porous ingrowth material 112, to a surface 111 of an insert to form a bonded insert 110. As used herein, "heat bonding" refers to a bonding process that utilizes temperatures above room temperature to bond two elements together without significant liquefaction of the material of either element. Exemplary heat bonding techniques include, but are not limited to, diffusion bonding, which utilizes relatively low temperatures and high pressures, and sintering, which utilizes relatively high temperatures and low pressures. Another heat bonding technique that may be utilized includes covering one or both of the elements to be joined with a third material, such as polyether ether ketone, which is melted to join the elements together. Many different type of other heat bonding techniques are known, depending on the material(s) of the elements being bonded together, so further description is omitted for brevity.

The bonded insert 110 may have a bare portion 114, such as a flange 115, that is placed 402 in an opening 102, 302 formed in a material, such as material of the base/implant body 101, 301 of the implant 100. As previously described, the bare portion 114 is not bonded to the porous material 112. The bare portion 114 is heat bonded 403 to the material to bond the bonded insert 110 to the material, which can result in the implant 100, 300 being formed with the bonded inserts 110. Alternatively, the bare portion 114 of the bonded insert 110 may be covered in porous material and heat bonded to the material to bond the bonded insert 110 to the material.

Forming the implant 100, 300 according to the previously described method 400 can result in several efficiencies. In known techniques, inserts, such as posts, are generally formed in the implant during casting or, alternatively, by machining the posts directly into a wrought, forged, or cast implant. Once the post(s) are formed, the porous ingrowth material is bonded to the post(s), which requires clamping the material to the post(s) and implant during bonding. This process is difficult and time-consuming due to the relatively small dimensions of the posts as well as the difficulty in properly clamping and holding the porous material to the posts without causing damage or rejection of the part.

The method 400 described herein, on the other hand, produces bonded inserts 110 that are heat bonded to the material of the implant 100, 300. The bonded inserts 110 may be formed in relatively large batches by placing several unbonded inserts with clamped porous ingrowth material into an oven for diffusion bonding. After the unbonded inserts and porous ingrowth material 112 have "cooked" at a sufficient time and temperature to achieve heat bonding, the formed bonded inserts 110 can be removed from the oven. The bonded inserts 110 are then ready to be bonded to a base/implant body 101, 301 by heat bonding. Thus, a large number of ready-made bonded inserts 110 can be stored on-site to form implants 100, 300 with, for example, multiple pegs when needed. It has been found that the heat bond between the bonded insert 110 and the material of the implant 100, 300 is at least strong enough to exceed the feature strength requirement for many medial implants. Further, in some embodiments a bare post can be bonded to the base/implant body 101, 301 before applying porous material to the bare post by, for example, plasma spray or other methods to provide posts with porous material on implant components that are not easily fabricated with porous components. Thus, implants formed according to the present disclosure can be produced significantly faster than using known techniques without impairing strength or durability requirements for a wide variety of medical implants.

The method 400 also allows for rapid formation of different implant designs. Many implants are known with different numbers of pegs and peg locations. By utilizing the method 400 disclosed herein, different implant styles with different numbers of pegs and peg locations can be formed with the ready-made bonded inserts 110 by forming 404 a desired opening pattern in material of a base/implant body 101, 301 to form at least the opening 102, 302, placing 402 the bare portion(s) 114 of the bonded insert(s) 110 in the formed opening(s) 102, 302, and heat bonding 403 the bare portion(s) 114 to the material to bond the bonded insert(s) 110 to the material and form the implant. Implant blanks, which have the general shape of the final implant but not the opening(s), may be stored on-site. The implant may then be formed by forming 404 one or more openings at the desired locations in an implant blank before placing the bare portion (s) 114 of the bonded insert(s) 110 in the opening(s) 102, 302 and heat bonding 403. It should thus be appreciated that the method 400 provided in accordance with the present disclosure can be readily adapted to form many different types of implants using ready-made bonded inserts and implant blanks.

Figure 5:
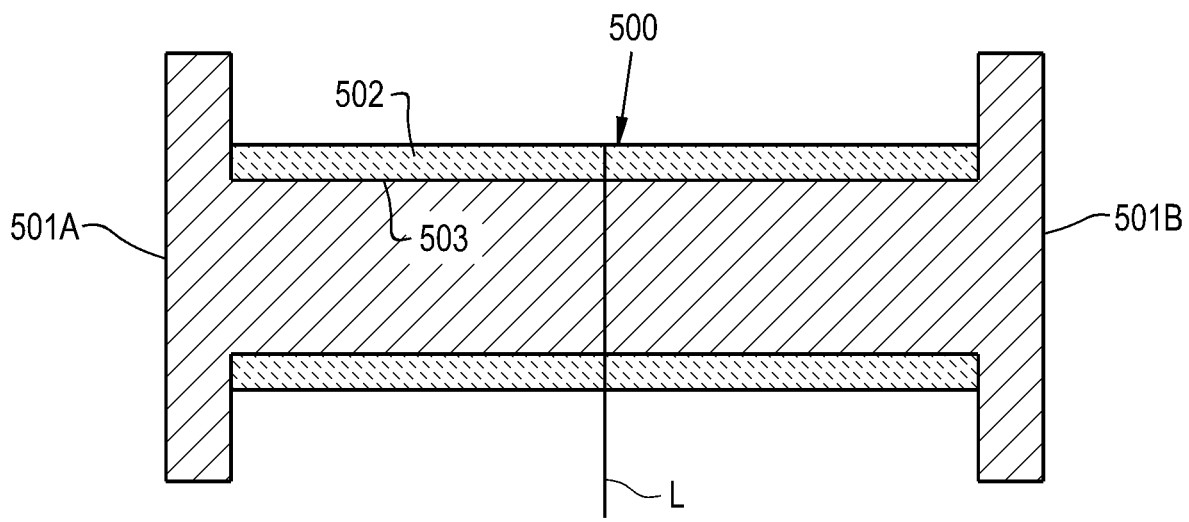
FIG. 5 is a cross-sectional view of an exemplary embodiment of a bonded insert assembly for producing a pair of bonded inserts, provided according to the present invention.

In some embodiments, and referring now to FIG. 5, the bonded insert 110 is formed from a bonded insert assembly 500. The bonded insert assembly 500 may include a pair of flanged ends 501A, 501B, representing bare portions, and porous ingrowth material 502 bonded to a surface 503 between the flanged ends 501A, 501B. The porous ingrowth material 502 is heat bonded to the surface 503 of the bonded insert assembly 500. After heat bonding, the bonded insert assembly 500 may be separated at a cleavage line L to form two individual bonded inserts each including a respective one of the flanged ends 501A, 501B. It should thus be appreciated that the bonded inserts 110 provided in accordance with the present disclosure can be rapidly manufactured to further decrease the amount of time needed to produce an implant according to the present disclosure.

Figure 6:
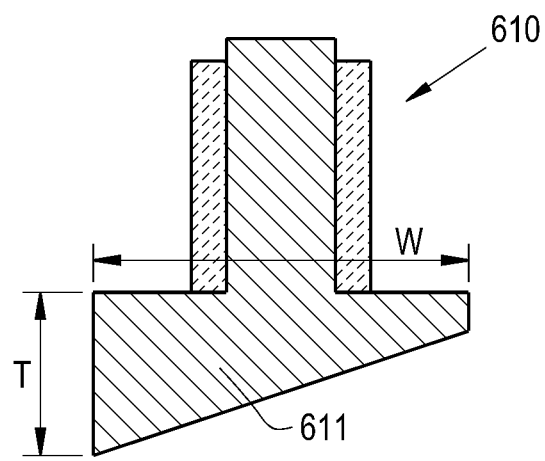
FIG. 6 is a cross-sectional view of an exemplary embodiment of a bonded insert including a tapered surface, provided according to the present invention.

In some embodiments, and referring now to FIG. 6, a bare portion 611 of a bonded insert 610 is fully or partially tapered and has a varying thickness T along a width W of the bare portion 611. Such a shape may help heat bond the insert 610 to, for example, a surface that is not flat, which is relatively difficult to do using previously known methods. Thus, the present disclosure also provides ways of forming implants that have differing shapes in a manner that is less difficult, and thus less costly, than known methods.

Figure 7:
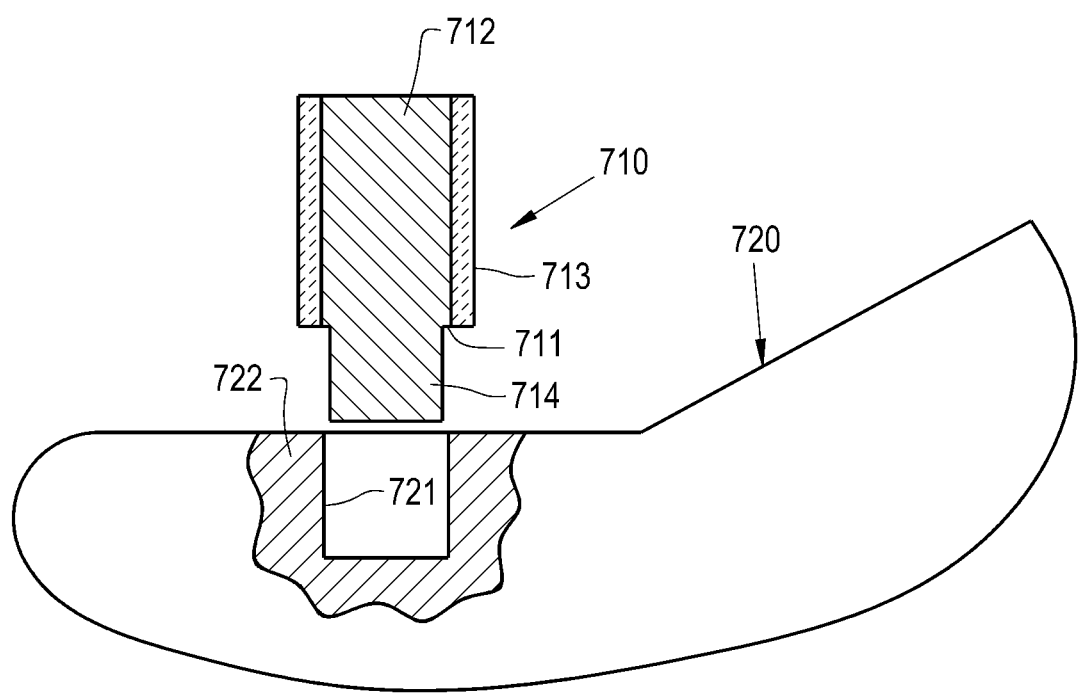
FIG. 7 is a partially exploded cross-sectional view of an exemplary embodiment of an orthopaedic implant including a bonded insert having a shoulder, provided according to the present invention.

Referring now to FIG. 7, an exemplary embodiment of another bonded insert 710 that may be used to form an implant is illustrated. As can be seen, the bonded insert 710 does not have a flanged end, like previously described bonded inserts 110, but instead has a shoulder 711 between a portion 712 of the insert 710 bonded to a porous ingrowth material 713 and a bare portion 714 of the insert 710 that is placed in an opening 721 of material 722 of an implant body 720. It should be appreciated that the illustrated implant body 720 is exemplary only, and the bonded insert 710 may be used to form a variety of different orthopaedic implants and/or components of orthopaedic implants, including but not limited to a total knee implant femoral component, a total knee implant tibial component, a partial knee implant component, a glenoid implant, etc. The shoulder 711 may be formed, for example, at the interface between the portion 712 that has the porous ingrowth material 713 bonded thereto and the bare portion 714, with the shoulder 711 having an increased width relative to the bare portion 714 due to the bonded porous ingrowth material 713. The bare portion 714 of the insert 710 is heat bonded to material 722 of the implant body 720, and the porous ingrowth material 713 may cover the opening 721 after heat bonding, similar to previously described bonded inserts. In some embodiments, the bare portion 714 of the insert 710 may include threads 715 that thread into corresponding threads 723 of the opening 721 to form a mechanical interlock prior to heat bonding the bare portion 714 to the implant body 720.

Figure 8:
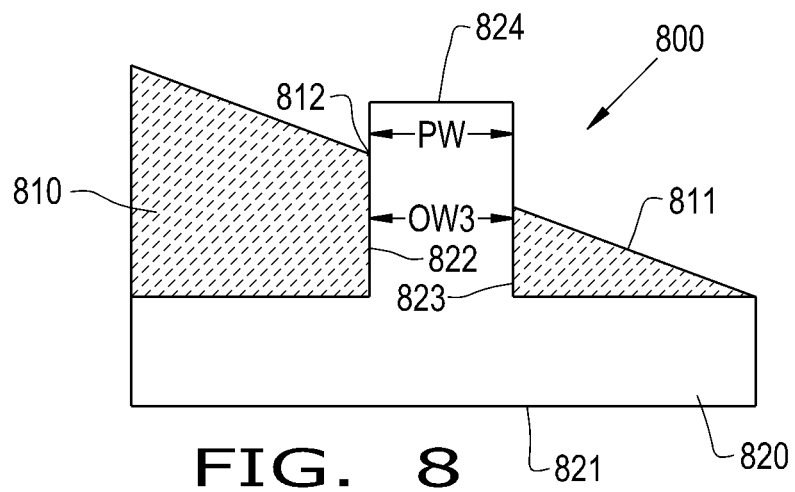
FIG. 8 is a cross-sectional view of an exemplary embodiment of an orthopaedic implant including a bonded insert with a porous ingrowth material having a complex outer surface.
Figure 9:
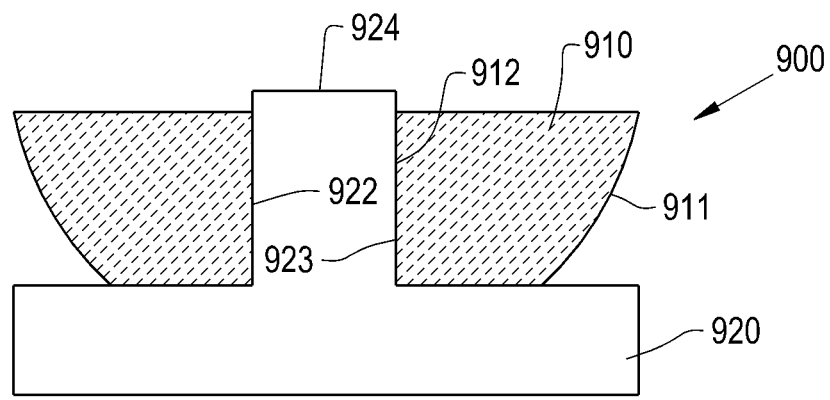
FIG. 9 is a cross-sectional view of another exemplary embodiment of an orthopaedic implant including a bonded insert with a porous ingrowth material having a complex outer surface.
Figure 10:
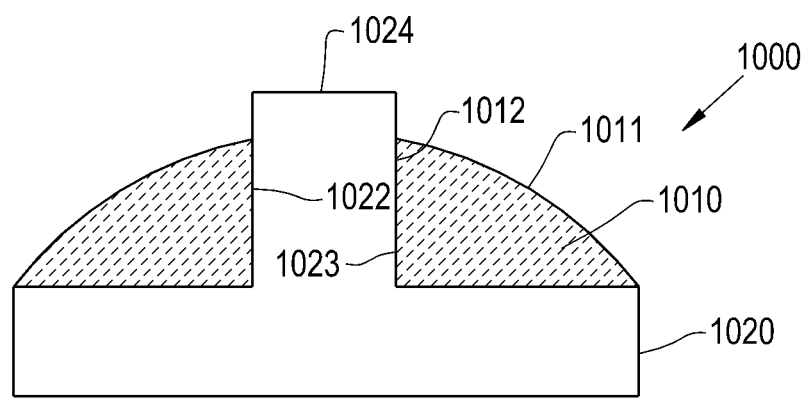
FIG. 10 is a cross-sectional view of yet another exemplary embodiment of an orthopaedic implant including a bonded insert with a porous ingrowth material having a complex outer surface.

In some exemplary embodiments, and referring now to FIGS. 8-10, an orthopaedic implant 800, 900, 1000 is provided that includes a complex component 810, 910, 1010 with one or more complex outer surfaces 811, 911, 1011 coupled to an implant body 820, 920, 1020. As used herein, a "complex outer surface" is an outer surface that is not perpendicular or parallel with a corresponding opposite surface of the implant body 820, 920, 1020, which makes the components 810, 910, 1010 complex. In the embodiment illustrated in FIG. 8, for example, the complex outer surface 811 is a tapered surface that is not parallel and/or perpendicular to a respective opposite surface 821, which may be a bottom surface, of the implant body 820. Due to the complex outer surface 811 being complex and not parallel or perpendicular to the respective opposite surface 821, it is very difficult to bond the complex component 810 to the implant body 820 using traditional methods, which usually include clamping, because there is little surface area for the clamps to engage for compressing the complex component 810 and the implant body 820 together. In some embodiments, the complex components 810, 910, 1010 comprise a solid material, i.e., a material with a porosity of less than 10%. However, it should be appreciated that the complex components 810, 910, 1010 may also, or alternatively, comprise a porous ingrowth material that forms the components 810, 910, 1010 and/or is attached to the components as a discrete porous layer 813, 913, 1013, as illustrated.

To address the issues of known methods for forming the orthopaedic implant 800, the complex component 810 may be placed in contact with at least one bonding surface of the implant body 820, illustrated as two bonding surfaces 822, 823, and heat bonded to the bonding surface(s) 822, 823 to bond the complex component 810 to the implant body 820. As illustrated, the bonding surfaces 822, 823 may be part of an extension, illustrated as a post 824, that extends from the implant body 820. The complex component 810 may, for example, be formed with a machined opening 812 extending through the complex outer surface 811 and defining an opening width OW3 that is approximately the same, if not slightly smaller, than a post width PW of the post 824. The complex component 810 may be slid over the implant body 820 so the post 824 resides within the opening 812 and, in some embodiments, the machined opening 812 may have threads 814 formed therein that thread onto corresponding threads 825 of the post 824 and form a mechanical interlock. Once the complex component 810 is placed so the post 824 is disposed in the opening 812, with or without forming a press fit or other mechanical interlock, the complex component 810 and the implant body 820 can be heat bonded together to firmly bond the complex component 810 to the implant body 820. In this respect, the complex component 810 and the implant body 820 can both be separately formed using traditional fabrication methods, such as machining, before being bonded together using heat bonding.

It should be appreciated that while the implant body 820 is illustrated and described as including the post 824 with the bonding surfaces 822, 823, in some embodiments the complex component 810 includes an extension, such as a post, and the implant body 820 includes the opening in which the extension is disposed before heat bonding. Alternatively, the complex component 810 and/or the implant body 820 may include multiple openings and/or extensions that fit together before heat bonding. Further, while the orthopaedic implant 800 illustrated in FIG. 8 is illustrated in the embodiment of a shoulder implant, other types of orthopaedic implants may be produced in a similar manner according to the present invention, including but not limited to total knee implants, partial knee implants, tibial implants, etc. It should thus be appreciated that a variety of different orthopaedic implants including a porous ingrowth material having at least one complex outer surface may be produced according to the present invention.

Referring specifically now to FIG. 9, another exemplary embodiment of an orthopaedic implant 900 provided according to the present invention is illustrated that has a complex component 910 with a complex outer surface 911 that is curved, rather than tapered. The orthopaedic implant 1000 illustrated in FIG. 10 similarly includes a complex component 1010 with a complex outer surface 1011 that is curved, but the complex component 1010 is inverted compared to the complex component 910. Similarly to the previously described complex component 810, the complex components 910, 1010 may comprise a solid material and/or a porous ingrowth material, which may be bonded to the complex components 910, 1010 as the previously described porous layer 913, 1013. Both of the orthopaedic implants 900, 1000 may be produced similarly to the previously described orthopaedic implant 800 by placing an extension, illustrated as posts 924, 1024, of the respective implant body 920, 1020 in an opening 912, 1012, with or without threads, formed in the complex component 910, 1010, by, e.g., machining, so the complex component 910, 1010 comes in contact with one or more bonding surfaces 922, 923, 1022, 1023 of the implant body 920, 1020, which may be part of the extension 924, 1024, and heat bonding the complex component 910, 1010 to the bonding surfaces 922, 923, 1022, 1023.

As can be appreciated from FIGS. 9 and 10, it would be very difficult to form the orthopaedic implants 900, 1000 using known manufacturing methods, which include clamping, due to the curvature of the complex outer surfaces 911, 1011. Forming the orthopaedic implants 900, 1000 according to the present invention, on the other hand, is relatively easy, and thus economical, and can reliably form the orthopaedic implants 900, 1000 with strength values that are acceptable for implantation. It should thus be appreciated that many different types of orthopaedic implants may be produced according to the present invention in an economical way.

Figure 11:
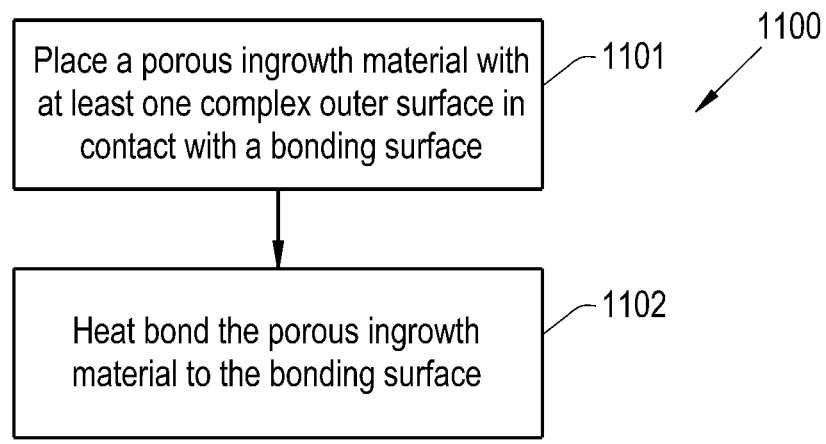
FIG. 11 is a flow chart illustrating another exemplary embodiment of a method of forming an orthopaedic implant with a porous ingrowth material having a complex surface, provided according to the present invention.

Referring now to FIG. 11, an exemplary embodiment of a method 1100 for forming an orthopaedic implant, such as any of the previously described orthopaedic implants 800, 900, 1000, provided according to the present invention is illustrated. The method 1100 includes placing 1101 a porous ingrowth material 810, 910, 1010, which has at least one complex outer surface 811, 911, 1011, in contact with at least one bonding surface 822, 823, 922, 923, 1022, 1023 of an implant body 820, 920, 1020. The bonding surface(s) 822, 823, 922, 923, 1022, 1023 may be part of an extension, such as a post 824, 924, 1024, and placed 1101 in a respective opening 812, 912, 1012 formed in the porous ingrowth material 810, 910, 1010. The porous ingrowth material 810, 910, 1010 is heat bonded 1102 to the bonding surface(s) 822, 823, 922, 923, 1022, 1023 to bond the porous ingrowth material 810, 910, 1010 to the implant body 820, 920, 1020, forming the orthopaedic implant 800, 900, 1000. As previously described, the complex outer surface(s) 811, 911, 1011 may be a tapered surface and/or a curved surface.

Figure 12:
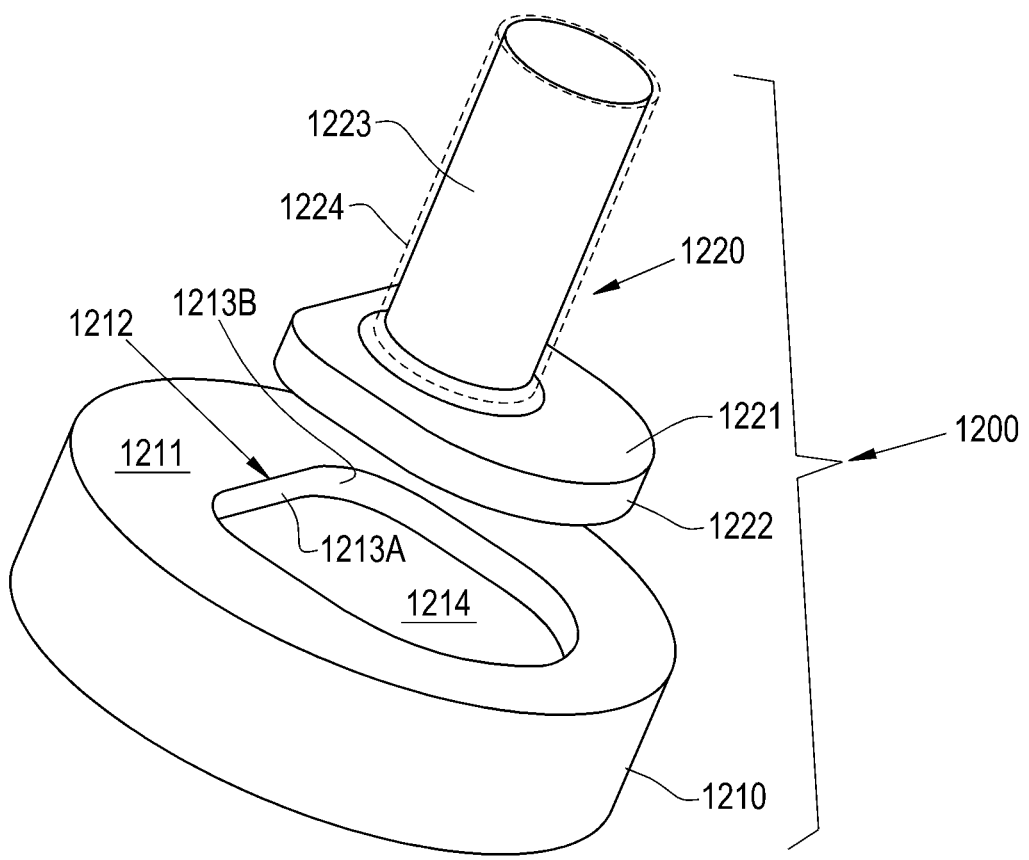
FIG. 12 is an exploded view of an exemplary embodiment of an orthopaedic implant including an implant body and a mating part bonded to the implant body, provided according to the present invention.
Figure 13:
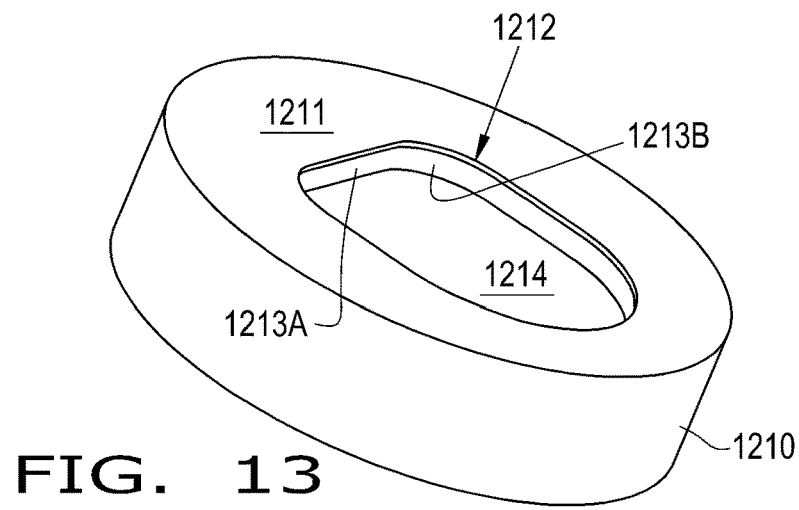
FIG. 13 is a perspective view of the implant body of FIG. 12 with a plurality of walls defining an opening.
Figure 14:
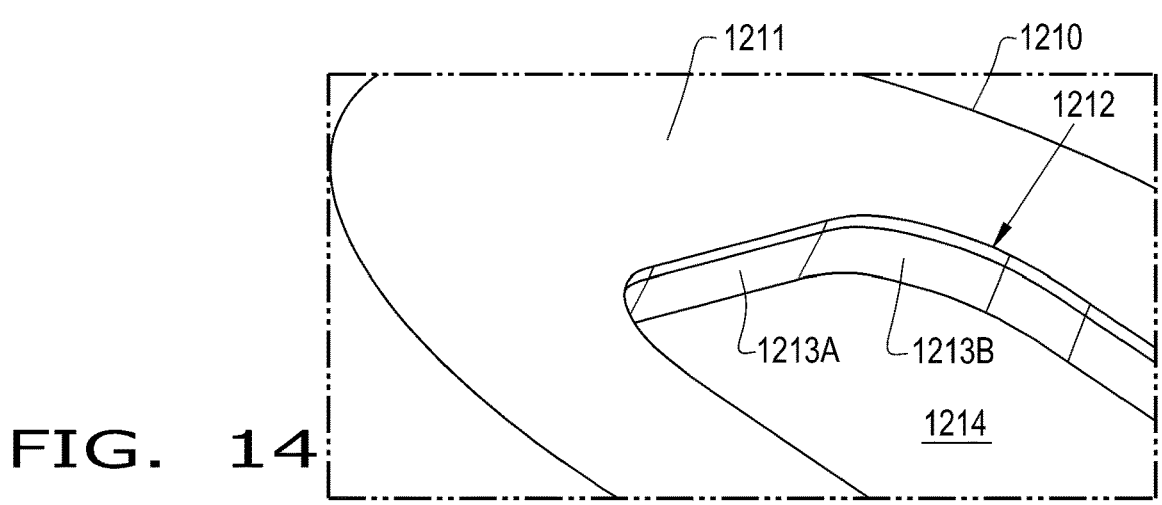
FIG. 14 is a close-up perspective view of the implant body of FIGS. 12-13.

While previously described orthopaedic implants include a porous ingrowth material, exemplary embodiments provided according to the present invention may be provided that do not necessarily include a porous ingrowth material. Referring specifically now to FIGS. 12-14, an exemplary embodiment of an orthopaedic implant 1200 is illustrated that includes an implant body 1210 and a mating part 1220 that is bonded to the implant body 1210. While the implant body 1210 and the mating part 1220 are illustrated in the shape of a shoulder implant, it should be appreciated that the orthopaedic implant may be formed as other type of implants, such as total or partial knee implants.

The implant body 1210 includes a surface 1211 with an opening 1212 formed therein. The implant body 1210 may be formed by any suitable manufacturing method, such as, but not limited to, casting and/or machining. The opening 1212 may be formed in the surface 1211 by machining, for example. The opening 1212 is defined by a plurality of walls 1213A, 1213B, which may extend from a bottom surface 1214 defining a bottom of the opening 1212. In other words, the opening 1212 is not an open bottom opening that extends through the implant body 1210, but has a closed bottom. As illustrated in FIGS. 13 and 14, the walls 1213A, 1213B may extend perpendicularly from the bottom surface 1214, which may be parallel to the surface 1211 in which the opening 1212 is formed, so the walls 1213A, 1213B extend perpendicularly to both the surface 1211 of the implant body 1210 and the bottom surface 1214 of the opening 1212. The opening 1212 is illustrated as having a D-shaped perimeter formed by the walls 1213A, 1213B, with some of the walls 1213A being planar and some of the walls 1213B being curved. However, it should be appreciated that the opening 1212 may be formed with any suitable shape for heat bonding the mating part 1220 to the implant body 1210, as will be described further herein.

The mating part 1220 includes a bonding portion 1221 that is placed in the opening 1212 and heat bonded to the implant body 1210 to form the orthopaedic implant 1200. The mating part 1220 may be formed by any suitable method such as, but not limited to, casting and/or machining. As can be appreciated from FIG. 12, the bonding portion 1221 has a shape that is similar to the opening 1212. Peripheral walls 1222 of the bonding portion 1221 may be in close proximity to and/or abutting the walls 1213A, 1213B defining the opening 1212 when the bonding portion 1221 is placed in the opening 1212. In some embodiments, the bonding portion 1221 is shaped and sized so the peripheral walls 1222 all come into contact with the walls 1213A, 1213B defining the opening 1212 when the bonding portion 1221 is placed in the opening 1212. Material of the peripheral walls 1222 is heat bonded with material of the walls 1213A, 1213B to bond the mating part 1220 to the implant body 1210, forming the orthopaedic implant 1200. The heat bonding may include, for example, diffusion bonding and/or sintering.

In some embodiments, the mating part 1220 comprises a post assembly including a post 1223 that extends from the bonding portion 1221. The post 1223 may, for example, extend perpendicularly from the bonding portion 1221 and have a cylindrical shape. The mating part 1220 may be completely bare of porous ingrowth material, i.e., have no porous ingrowth material bonded to the mating part 1220, or, alternatively, may have one or more portions of porous ingrowth material 1224 (illustrated in dashed lines) bonded thereto, such as to the post 1223. If porous ingrowth material 1224 is included, the porous ingrowth material 1224 may also be heat bonded to the mating part 1220.

Figure 15:
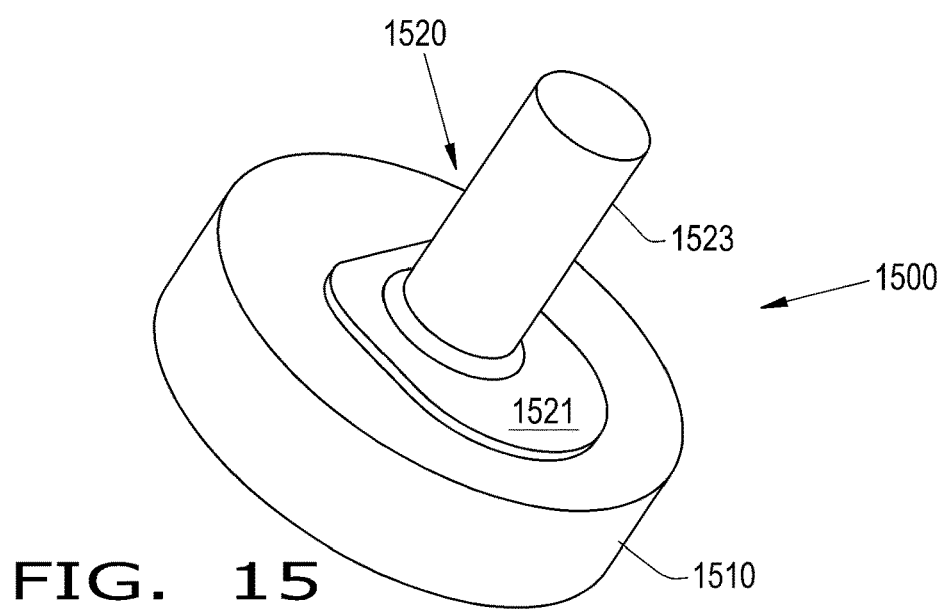
FIG. 15 is a perspective view of another exemplary embodiment of an orthopaedic implant including an implant body and a mating part prior to bonding of the mating part to the implant body, provided according to the present invention.
Figure 16A:
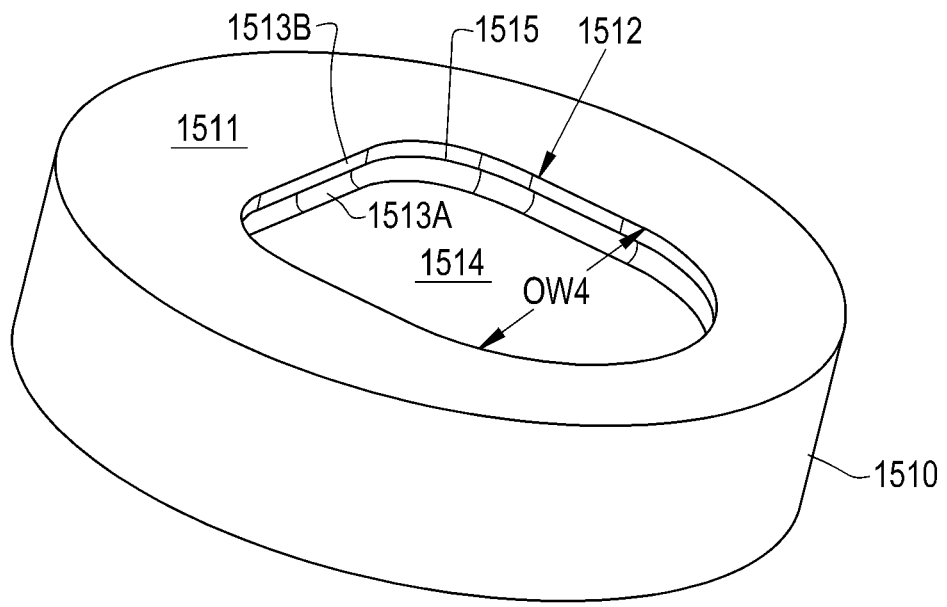
FIG. 16A is a perspective view of the implant body of FIG. 15.
Figure 16B:
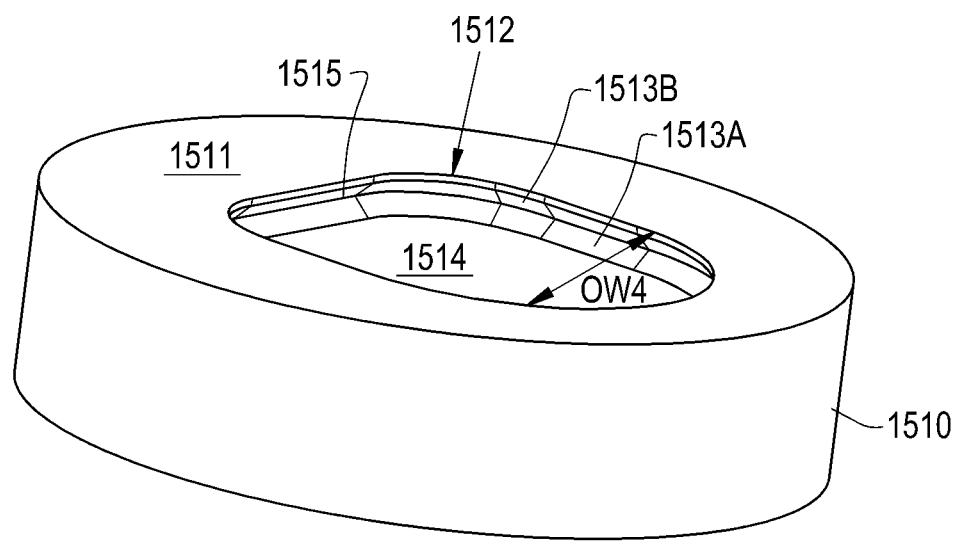
FIG. 16B is another perspective view of the implant body of FIGS. 15 and 16A.

In certain instances, additional bonding forces between parts forming an orthopaedic implant may be desired. Referring now to FIGS. 15, 16A, and 16B, another exemplary embodiment of an orthopaedic implant 1500 provided according to the present invention is illustrated. The orthopaedic implant 1500 includes an implant body 1510 and a mating part 1520 that has a bonding portion 1521 heat bonded to the implant body 1510. The illustrated mating part 1520 is similar to the previously described mating part 1220 and may comprise, for example, a post assembly having a post 1523.

Referring specifically now to FIGS. 16A and 16B, the implant body 1510 is illustrated by itself in greater detail. Similar to the previously described implant bodies, the implant body 1510 has a surface 1511 with an opening 1512 formed therein. The bonding portion 1521 of the mating part 1520 is disposed in the opening 1512 and heat bonded to the implant body 1510. Unlike the previously described implant bodies, which were illustrated and described with openings defining a constant opening width, the opening 1512 is defined by a plurality of walls 1513A, 1513B that may extend from a bottom surface 1514 in a non-perpendicular manner so the opening 1512 defines a variable opening width OW4, which may vary based on a distance from the bottom surface 1514. The walls 1513A may connect to the bottom surface 1514 and the walls 1513B may connect to the walls 1513A and terminate at the surface 1511 in which the opening 1512 is formed.

The opening width OW4 may be a first value at a first distance from the bottom surface 1514 that is essentially zero, i.e., the first value of the opening width OW4 is defined at the bottom surface 1514. The opening width OW4 at the first distance may be less than the opening width OW4 at a second distance from the bottom surface 1514 that is greater than the first distance. This may be seen in FIG. 16A especially, with the walls 1513A extending so the opening width OW4 increases with distance from the bottom surface 1514. The opening width OW4 may increase to a maximum value at the second distance from the bottom surface 1514 where the walls 1513A, 1513B meet. The opening width OW4 may then decrease at a third distance from the bottom surface 1514, which is greater than the second distance and corresponds to the walls 1513B extending such that the opening width OW4 decreases with greater distance from the bottom surface 1514. An undercut 1515 may be formed at the meeting point of the walls 1513A, 1513B, i.e., at a location that is between the second distance and the third distance from the bottom surface 1514, with the undercut 1515 representing a transition region between the opening width OW4 increasing or decreasing with increasing distance from the bottom surface 1514.

Forming the undercut 1515 in the implant body 1510 allows a mechanical interlock to be formed during heat bonding of the mating part 1520 and the implant body 1510. During diffusion bonding, for example, material from a bonding portion 1521 of the mating part 1520 will deform into the walls 1513A, 1513B of the implant body 1510 due to the relatively high temperatures and pressure without significant liquefaction of the material of the bonding portion 1521. As the material deforms into the walls 1513A, 1513B, material will fill the formed undercut 1515. Due to the opening width OW4 decreasing at a further distance from the bottom surface 1514 past the undercut 1515, i.e., closer toward the surface 1511, material from the bonding portion 1521 that deforms into the undercut 1515 will form an interference fit between the bonding portion 1521 and the walls 1513B, making it more difficult to pull the mating part 1520 out of the opening 1512. Thus, forming the undercut 1515 in the implant body 1510 allows the orthopaedic implant 1500 to be formed with both heat bonding and a mechanical interlock between the implant body 1510 and the mating part 1520, strengthening the bond between the implant body 1510 and the mating part 1520.

Figure 17:
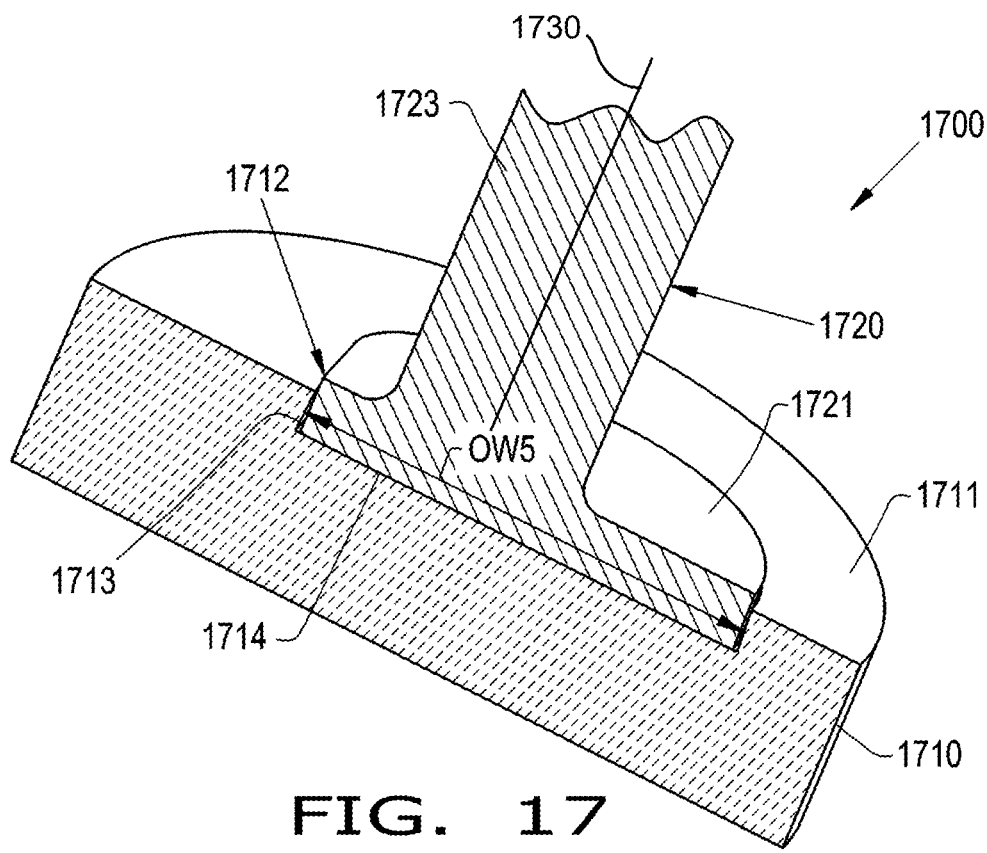
FIG. 17 is a cross-sectional view of another exemplary embodiment of an orthopaedic implant including an implant body and a mating part prior to bonding of the mating part to the implant body, provided according to the present invention.
Figure 18:
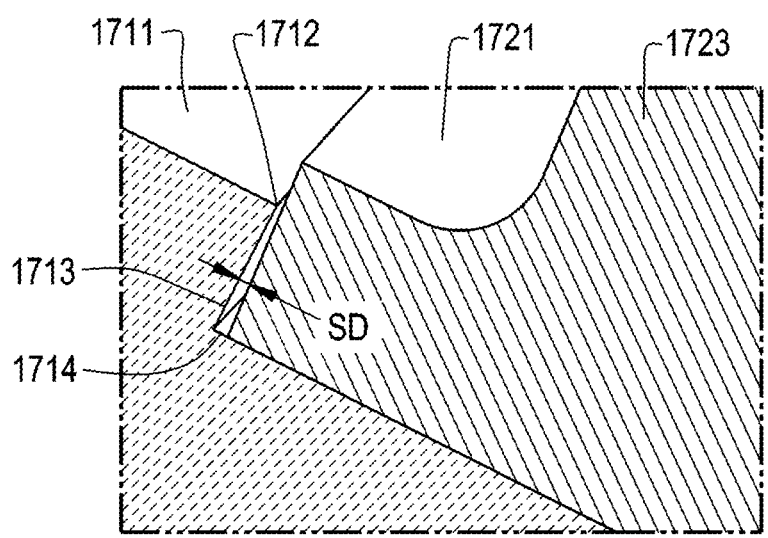
FIG. 18 is another cross-sectional view of the orthopaedic implant of FIG. 17.
Figure 19:
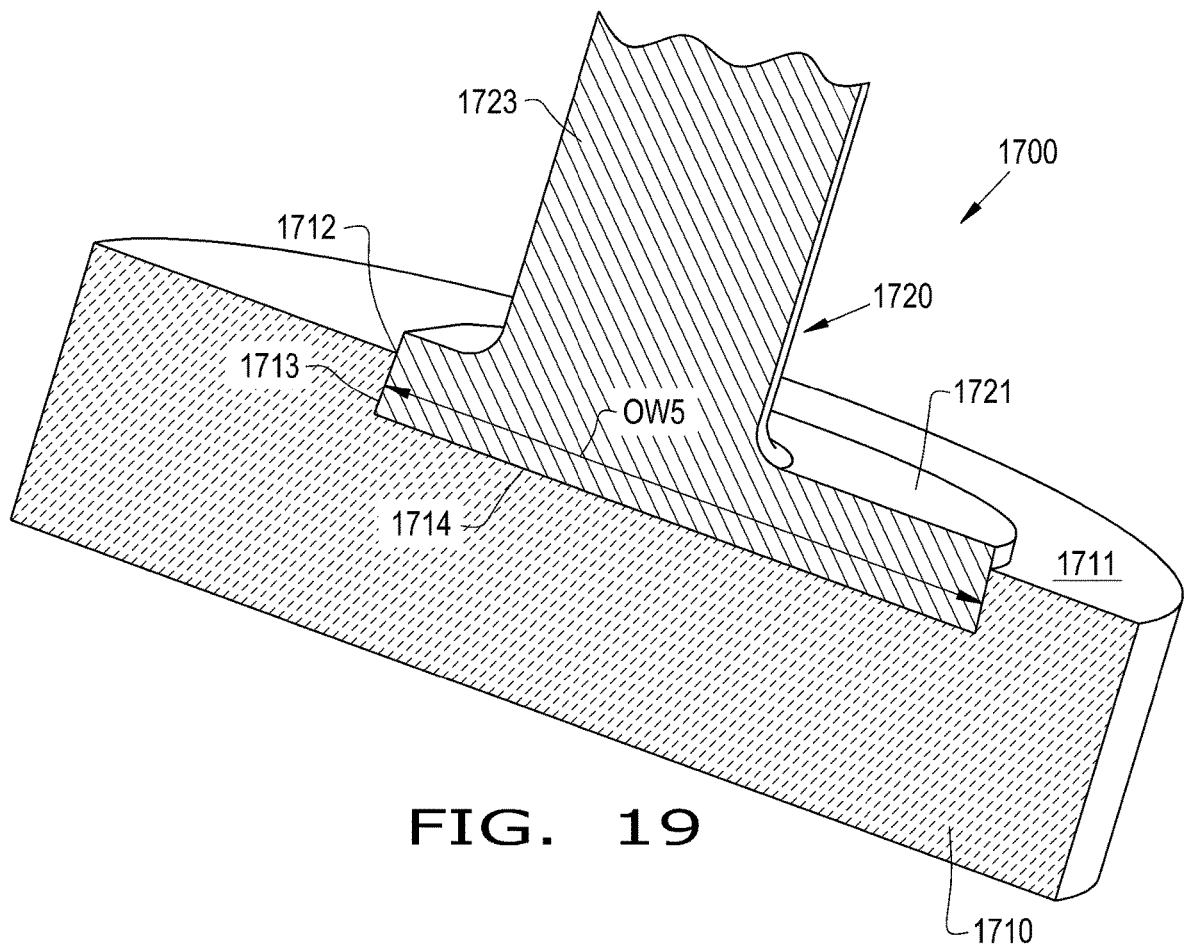
FIG. 19 is a cross-sectional view of the orthopaedic implant of FIGS. 17-18 after bonding the mating part to the implant body.

Referring now to FIGS. 17-19, another exemplary embodiment of an orthopaedic implant 1700 provided according to the present invention is illustrated. The orthopaedic implant 1700 includes an implant body 1710 with a surface 1711 having a variable width opening 1712 formed therein and a mating part 1720 having a bonding portion 1721 disposed in the opening 1712 and heat bonded to the implant body 1710. The mating part 1720 may be similar to the previously described mating parts 1220, 1520 and comprise a post assembly including a post 1723.

The opening 1712 may be defined by a plurality of walls 1713 that extend from a bottom surface 1714 defining a bottom of the opening 1712. As especially illustrated in FIG. 18, the walls 1713 may extend from the bottom surface 1714 such that the opening 1712 defines an opening width OW5 that decreases with an increasing distance from the bottom surface 1714. In other words, the opening width OW5 may be greater at a first distance from the bottom surface 1714 than the opening width OW5 at a second distance from the bottom surface 1714 that is greater than the first distance. The opening width OW5 may decrease with increasing distance from the bottom surface 1714 at a constant rate, i.e., a constant angle, or may decrease at a variable rate. Further, as shown in FIG. 17, the top surface of the implant body 1710 is perpendicular relative to a longitudinal axis 1730 of the post 1723, and a top surface of the bonding portion 1721 of the mating part 1720 is perpendicular relative to the longitudinal axis 1730 of the post 1723.

Referring specifically now to FIG. 18, it is illustrated that the bonding portion 1721 of the mating part 1720 may abut against at least one of the walls 1713 when placed in the opening 1712. As illustrated, the abutment between the bonding portion 1721 and the wall(s) 1713 may be adjacent to the surface 1711 of the implant body 1710, where the opening width OW5 may be a minimum. The bonding portion 1721 may define a constant width throughout and a variable separation distance SD from the wall(s) 1713 when placed in the opening 1712. The variable separation distance SD may vary, for example, in an endpoint-inclusive range of between 0.0001 inches and 0.125 inches, such as 0.005 inches to 0.020 inches. While the variable separation distance SD is illustrated and described as being due to the variable opening width OW5 and the constant width of the bonding portion 1721, in some embodiments the bonding portion 1721 has a variable width that controls or contributes to the variable separation distance between the bonding portion 1721 and the walls 1713.

By providing the variable separation distance SD between the walls 1713 defining the opening 1712 and the bonding portion 1721, an interference fit can be formed between the implant body 1710 and the mating part 1720 during heat bonding. Referring specifically now to FIG. 19, which illustrates the orthopaedic implant 1700 following heat bonding of the mating part 1720 to the implant body 1710, material from the bonding portion 1721 has deformed into the gap between the bonding portion 1721 and the walls 1713 and filled the gap between the bonding portion 1721 and the walls 1713. Due to the opening width OW5 of the opening 1712 decreasing with increasing distance from the bottom surface 1714, i.e., toward the surface 1711, an interference fit is formed between the deformed material of the bonding portion 1721 and the walls 1713 that makes it more difficult for the mating part 1720 to be pulled out of the opening 1712. Keeping the separation distance SD to be no more than, for example, 0.125 inches ensures that material from the bonding portion 1721 deforms sufficiently to come into contact with the walls 1713 and form the interference fit. Thus, the orthopaedic implant 1700 has a mating part 1720 that is both heat bonded and mechanically interlocked with the implant body 1710, increasing the strength of the bond between the mating part 1720 and the implant body 1710.

Figure 20:
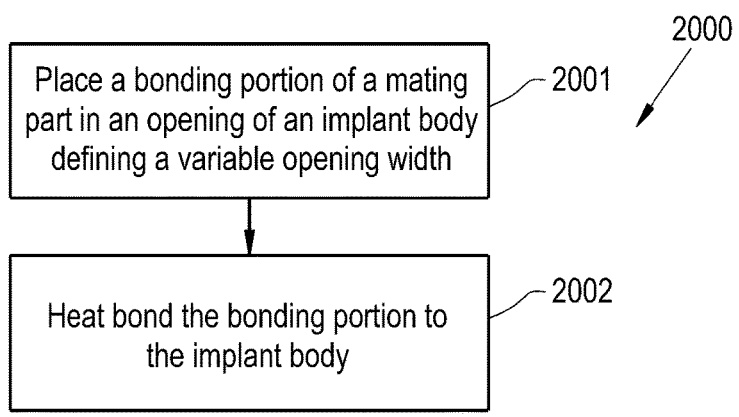
FIG. 20 is a flow chart illustrating an exemplary embodiment of a method of forming an orthopaedic implant including an implant body and a mating part bonded to the implant body, provided according to the present invention.

Referring now to FIG. 20, an exemplary embodiment of a method 2000 of forming an orthopaedic implant 1500, 1700 provided according to the present invention is illustrated. The method 2000 includes placing 2001 a bonding portion 1521, 1721 of a mating part 1520, 1720 in an opening 1512, 1712 formed in an implant body 1510, 1710 and defining a variable opening width OW4, OW5. The bonding portion 1521, 1721 is heat bonded 2002 to the implant body 1510, 1710 to bond the mating part 1520, 1720 to the implant body 1510, 1710 and form the orthopaedic implant 1500, 1700. In some embodiments, the heat bonding 2002 includes diffusion bonding. In some embodiments, the implant body 1510 has an undercut 1515 formed therein, as previously described, and material of the bonding portion 1521 flows into the undercut 1515 during heat bonding 2002 to form an interference fit between the bonding portion 1521 and walls 1513A, 1513B defining the opening 1512.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of forming an orthopaedic implant, comprising:
    placing a bonding portion of a mating part in an opening formed in an implant body, the opening defining a variable opening width, the implant body including a first wall that forms a bottom surface of the opening, the bottom surface of the opening of the implant body being positioned directly below a bottom surface of the bonding portion, the mating part including a post extending perpendicularly from the bonding portion, the implant body including a plurality of second walls defining the opening width and extending from the bottom surface of the opening of the implant body to a top surface of the implant body, the top surface of the implant body being perpendicular relative to a longitudinal axis of the post, a top surface of the bonding portion of the mating part being perpendicular relative to the longitudinal axis of the post; and
    heat bonding the bonding portion to a material to bond the mating part to the implant body.

2. The method of claim 1, wherein the opening width varies with a distance from the bottom surface of the implant body.

3. The method of claim 2, wherein the opening width at a first distance from the bottom surface is less than the opening width at a second distance from the bottom surface that is greater than the first distance and the opening width at a third distance from the bottom surface is less than the opening width at the second distance from the bottom surface to form an undercut, the third distance being greater than the second distance.

4. The method of claim 3, wherein material of the bonding portion flows into the undercut during heat bonding to form an interference fit between the bonding portion and at least some of the walls.

5. The method of claim 4, wherein the heat bonding comprises diffusion bonding.

6. The method of claim 2, wherein the opening width at a first distance from the bottom surface is greater than the opening width at a second distance from the bottom surface that is greater than the first distance.

7. The method of claim 1, wherein the bonding portion abuts against at least one of the second walls and defines a variable separation distance from at least one of the second walls when placed in the opening, the variable separation distance defining a maximum separation distance of no more than 0.125 inches.

8. The method of claim 1, wherein the mating part comprises a post assembly comprising the post.

9. The method of claim 1, wherein, prior to the step of heat bonding, the bonding portion defines a shape that is similar to a shape of the opening.

10. The orthopaedic implant of claim 1, wherein the variable opening width decreases with an increasing distance from the bottom surface of the opening of the implant body, the plurality of second walls having an absence of a porous ingrowth material.

11. The orthopaedic implant of claim 1, wherein the material is polyether ether ketone.

* * * * *